US006190536B1

United States Patent
Lokhandwala et al.

(10) Patent No.: US 6,190,536 B1
(45) Date of Patent: Feb. 20, 2001

(54) CATALYTIC CRACKING PROCESS

(75) Inventors: Kaaeid A. Lokhandwala, Union City; Richard W. Baker, Palo Alto, both of CA (US)

(73) Assignee: Membrane Technology and Research, Inc., Menlo Park, CA (US)

( * ) Notice: Under 35 U.S.C. 154(b), the term of this patent shall be extended for 0 days.

(21) Appl. No.: 09/083,784

(22) Filed: May 22, 1998

(51) Int. Cl.[7] .............................. C07C 7/00; C07C 7/144; C07C 7/11
(52) U.S. Cl. .................... 208/103; 208/113; 208/100; 208/101; 208/102; 208/105; 585/818; 585/651; 585/920; 585/921; 585/809
(58) Field of Search ..................... 208/113, 100, 208/101, 102, 103, 105; 585/818, 651, 920, 921, 809

(56) References Cited

U.S. PATENT DOCUMENTS

| | | | |
|---|---|---|---|
| 4,230,463 | * 10/1980 | Henis et al. | 55/16 |
| 4,362,613 | 12/1982 | MacLean | 208/108 |
| 4,364,820 | * 12/1982 | DeGraff et al. | 208/101 |
| 4,367,135 | 1/1983 | Posey, Jr. | 208/108 |
| 4,548,619 | 10/1985 | Steacy | 55/16 |
| 4,654,063 | 3/1987 | Auvil et al. | 62/18 |
| 4,772,295 | 9/1988 | Kato et al. | 55/16 |
| 4,836,833 | 6/1989 | Nicholas et al. | 55/16 |
| 4,857,078 | 8/1989 | Watler | 55/16 |
| 4,892,564 | 1/1990 | Cooley | 55/16 |
| 4,925,459 | * 5/1990 | Rojey et al. | 155/16 |
| 4,963,165 | 10/1990 | Blume et al. | 55/16 |
| 5,015,268 | * 5/1991 | Ho | 55/16 |
| 5,053,067 | 10/1991 | Chretien | 62/24 |
| 5,082,481 | 1/1992 | Barchas et al. | 62/23 |
| 5,157,200 | 10/1992 | Mikkinen et al. | 585/803 |
| 5,199,962 | 4/1993 | Wijmans | 55/16 |
| 5,256,295 | 10/1993 | Baker et al. | 210/640 |
| 5,332,424 | 7/1994 | Rao et al. | 95/47 |
| 5,332,492 | 7/1994 | Maurer et al. | 208/340 |
| 5,354,547 | 10/1994 | Rao et al. | 423/650 |
| 5,360,533 | * 11/1994 | Tagamolila | 208/101 |
| 5,435,836 | 7/1995 | Anand et al. | 95/45 |

(List continued on next page.)

OTHER PUBLICATIONS

"Membrane Technology for Hydrocarbon Separation," Membrane Associates, Ltd. no month.
"Polymeric Gas Separation Membranes," Paul and Yampolskii (eds.)—no month.
H. Yamashiro, "Plant Uses Membrane Separation," Hydrocarbon Processing, Feb. 1985.
H. Yamashiro et al., "Hydrogen Purification with Cellulose Acetate Membranes," presented at Europe–Japan Congress on Membranes and Membrane Processes, Jun. 18–21, 1984.
J.M. Abrardo, "Hydrogen Technologies to Meet Refiners' Future Needs," Hydrocarbon Processing, Feb. 1995.
W.A. Bollinger et al., "Optimizing Hydrocracker Hydrogen," Chemical Engineering Progress, May 1984.
W.A. Bollinger et al., "Prism™ Separators Optimize Hydrocracker Hydrogen," presented at AIChE 1983 Summer National Meeting, Session No. 66, Aug. 29, 1983.
T. Haheri et al., "Scale–Up of Selective Surface Flow Membrane for Gas Separation," by Air Products and Chemicals—no month.

(List continued on next page.)

*Primary Examiner*—Walter D. Griffin
*Assistant Examiner*—Nadine Preisch
(74) *Attorney, Agent, or Firm*—J. Farrant

(57) ABSTRACT

Processes and apparatus for providing improved catalytic cracking, specifically improved recovery of olefins, LPG or hydrogen from catalytic crackers. The improvement is achieved by passing part of the wet gas stream across membranes selective in favor of light hydrocarbons over hydrogen.

53 Claims, 5 Drawing Sheets

U.S. PATENT DOCUMENTS

| | | | |
|---|---|---|---|
| 5,452,581 | | 9/1995 | Dinh et al. ................................. 62/24 |
| 5,507,856 | | 4/1996 | Rao et al. ................................. 95/50 |
| 5,634,354 | | 6/1997 | Howard et al. .......................... 62/624 |
| 5,670,051 | * | 9/1997 | Pinnau et al. .......................... 210/651 |
| 5,689,032 | | 11/1997 | Krause et al. .......................... 585/802 |
| 5,744,687 | * | 4/1998 | Ramachandran et al. ............ 585/829 |
| 5,785,739 | * | 7/1998 | Baker ........................................ 95/39 |
| 5,814,208 | * | 9/1998 | Menon et al. ........................ 208/113 |

OTHER PUBLICATIONS

M. Anand, "Novel Selective Surface Flow (SSF™) Membranes for the Recovery of Hydrogen Waste Gas Streams," by Air Products Inc., Report to DOE, Aug. 1995.

M. Anand et al., "Novel Selective Surface Flow (SSF™) Membranes for the Recovery of Hydrogen from Waste Gas Streams," Report by Air Products to DOE, Apr. 1996.

E.W. Funk et al., "Effect of Impurities on Cellulose Acetate Membrane Performance," AIChE Symposium Series, No. 250, vol. 82—no month.

N.N. Li, et al. "Membrane Separation Processes in the Petrochemical Industry," Report by Allied–Signal Engineered Materials Research Center to DOE, Sep. 30, 1997.

* cited by examiner

CATALYTIC CRACKING PROCESS

This invention was made in part with Government support under Contract No. DE-FG03-94ER81811 awarded by the Department of Energy. The Government has certain rights in this invention.

FIELD OF THE INVENTION

The invention relates to catalytic cracking of hydrocarbons. In particular, the invention relates to treatment of gases from catalytic crackers by membrane separation to recover olefins and hydrogen.

BACKGROUND OF THE INVENTION

Catalytic cracking is used in most U.S. refineries to increase gasoline yield from petroleum feedstocks. The catalytic cracker accepts diverse feedstocks, including heavy and light vacuum gas oil (VGO) from the vacuum distillation column, heavy coker gas oils, light gas oil from the atmospheric distillation column, solvent deasphalted oils, lube extracts and hydrocracker bottoms. The catalytic cracking operation breaks down the heavy molecules in these cuts to form lower boiling components for gasoline and heating and fuel oils. The cracking operation can be adjusted to meet fluctuating consumer demand for these products.

The dominant catalytic cracking process is fluid catalytic cracking (FCC), so called because the catalyst is in the form of fine grains that circulate through the reactor continuously in fluid-like flow. In the FCC process, preheated hydrocarbon feedstock is injected into a section of the reactor unit known as the riser. Hot catalyst flows upward through the riser, and the cracking reactions take place. Numerous products can be retrieved from the raw crackate. These range from hydrogen to heavy fuel oils.

The raw effluent from the reactor is passed into a large distillation column and fractionated, typically into four or five main streams. Each of these streams can be subjected to downstream treatment to separate and purify individual products. The overhead from the main column usually contains mostly $C_5$ and lighter hydrocarbons, with other contaminants, such as hydrogen, carbon dioxide, water vapor, hydrogen sulfide, ammonia, nitrogen and other trace materials. Because of the conditions under which the cracking takes place, this fraction contains substantial amounts of unsaturated hydrocarbons, particularly ethylene and propylene. The overhead stream is separated into overhead liquids, which form gasoline product, and overhead vapor, generally known as wet gas. The wet gas passes to the unsaturated gas treatment section, where various absorbers and distillation columns are used to recover additional gasoline components and $C_3/C_4$ hydrocarbons. The light gases remaining after treatment are sent to the fuel line.

Fuel gas from FCC units may represent as much as 3–4 wt % of the plant feedstock. A representative typical composition, by volume, is about 15–30% hydrogen, about 15–40% ethylene and propylene, about 5–20% $C_{3+}$ hydrocarbons and about 30–60% $C_1/C_2$ hydrocarbons. The demand for ethylene and propylene as chemical feedstocks is rising, as is the demand for hydrogen to supply the hydrogen-consuming units, such as hydrotreaters and crackers, in the refinery. In fact, most refineries currently operate with a hydrogen deficit, which would be reduced if more hydrogen could be recovered from ongoing operations. Thus, these fuel gas streams present the opportunity for additional recovery of needed and valuable materials, if cost-effective separation techniques can be found.

In addition, only a finite quantity of fuel gas is needed, so some plants are bottlenecked by over supply. In these bottleneck situations, reduction in the amount of fuel gas produced, and/or control of the Btu value of that gas by reducing the heavier hydrocarbon content, would enable throughput of the unit operations in the refinery train, such as hydrotreating or reforming, to be increased.

Hydrogen recovery techniques that have been deployed in refineries include, besides simple phase separation of fluids, pressure swing adsorption (PSA) and membrane separation. U.S. Pat. No. 4,362,613, to Monsanto, describes a process for treating the vapor phase from a high pressure separator in a hydrocracking plant by passing the vapor across a membrane that is selectively permeable to hydrogen. The process yields a hydrogen-enriched permeate that can be recompressed and recirculated to the hydrocracker reactor. U.S. Pat. No. 4,367,135, also to Monsanto, describes a process in which effluent from a low pressure separator is treated to recover hydrogen using the same type of hydrogen-selective membrane. U.S. Pat. No. 4,548,619, to UOP, shows membrane treatment of the overhead gas from an absorber treating effluent from benzene production. The membrane again permeates the hydrogen selectively and produces a hydrogen-enriched gas product that is withdrawn from the process. U.S. Pat. No. 5,053,067, to L'Air Liquide, discloses removal of part of the hydrogen from a refinery off-gas to change the dewpoint of the gas to facilitate downstream treatment. U.S. Pat. No. 5,157,200, to Institut Francais du Petrole, shows treatment of light ends containing hydrogen and light hydrocarbons, including using a hydrogen-selective membrane to separate hydrogen from other components. U.S. Pat. No. 5,689,032, to Krause/Pasadyn, discusses a method for separating hydrogen and hydrocarbons from refinery off-gases, including multiple low-temperature condensation steps and a membrane separation step for hydrogen removal. U.S. Pat. No. 5,332,492, to UOP, concerns treatment of effluent gases from catalytic reformers by cooling followed by PSA.

The use of certain polymeric membranes to treat off-gas streams in refineries is also described in the following papers: "Hydrogen Purification with Cellulose Acetate Membranes", by H. Yamashiro et al., presented at the Europe-Japan Congress on Membranes and Membrane Processes, June 1984; "Prism™ Separators Optimize Hydrocracker Hydrogen", by W. A. Bollinger et al., presented at the AIChE 1983 Summer National Meeting, August 1983; "Plant Uses Membrane Separation", by H. Yamashiro et al., in Hydrocarbon Processing, February 1985; and "Optimizing Hydrocracker Hydrogen" by W. A. Bollinger et al., in Chemical Engineering Progress, May 1984. These papers describe system designs uses cellulose acetate or similar membranes that permeate hydrogen and reject hydrocarbons. The use of membranes in refinery separations is also mentioned in "Hydrogen Technologies to Meet Refiners' Future Needs", by J. M. Abrardo et al. in Hydrocarbon Processing, February 1995. This paper points out the disadvantage of membranes, namely that they permeate the hydrogen, thereby delivering it at low pressure, and that they are susceptible to damage by hydrogen sulfide and heavy hydrocarbons.

A chapter in "Polymeric Gas Separation Membranes", D. R. Paul et al. (Eds.) entitled "Commercial and Practical Aspects of Gas Separation Membranes", by Jay Henis describes various hydrogen separations that can be performed with hydrogen-selective membranes.

In all of the above cases, the membranes used to perform the hydrogen/hydrocarbon separation are hydrogen-selective, that is, they permeate hydrogen preferentially over hydrocarbons and all other gases in the mix.

A difficulty that hampers the use of membrane separation systems of the type described above is the presence in off-gases of the heavier hydrocarbons, water vapor and hydrogen sulfide. These materials cause a variety of problems, including catastrophic collapse of the membranes. For example, a report by N. N. Li et al. to the Department of Energy ("Membrane Separation Processes in the Petrochemical Industry", Phase II Final Report, September 1987) presents data showing the effect of water vapor on membrane flux for cellulose acetate membranes, and concludes that "for relative humidities of 30% and higher, the flux decline is large, rapid, and irreversible". E. W. Funk et al. ("Effect of Impurities on Cellulose Acetate Membrane Performance", Recent Advances in Separation Techniques—III, AIChE Symposium Series, 250, Vol 82, 1986) advocate that "Moisture levels up to 20% RH appear tolerable but higher levels can cause irreversible membrane compaction". Similar or worse problems can occur if liquid hydrocarbons are allowed to come into contact with membranes surfaces, as well as glues or other components used in the membrane modules. Although the feed gas to the inlet of the membrane separation system may be comfortably above its dewpoint, as the gas travels along the modules and is depleted in the faster permeating hydrogen, the hydrocarbon content of the residue can quickly build up, raising the dewpoint temperature sufficiently for hydrocarbon condensation in the modules to take place. To avoid this, either the gas must be heated at least 10° C. above the highest dewpoint temperature that will be reached, or contaminants must be removed to a low level before the gas enters the membrane system. Literature from Membrane Associates Ltd., of Reading, England, shows and describes a design for pooling and downstream treating various refinery off-gases, including passing of the membrane permeate stream to subsequent treatment for LPG recovery.

Other references that describe membrane-based separation of hydrogen from gas streams in a general way include U.S. Pat. Nos. 4,654,063, 4,836,833, to Air Products, and U.S. Pat. No. 4,892,564, to Cooley.

U.S. Pat. No. 5,332,424, to Air Products, describes fractionation of a gas stream containing light hydrocarbons and hydrogen using an "adsorbent membrane". The membrane is made of carbon, and selectively adsorbs hydrocarbons onto the carbon surface, allowing separation between various hydrocarbon fractions to be made. Hydrogen tends to be retained in the membrane residue stream. Other Air Products patents that show application of carbon adsorbent membranes to hydrogen/hydrocarbon separations include U.S. Pat. Nos. 5,354,547; 5,435,836; 5,447,559 and 5,507,856, which all relate to purification of streams from steam reformers.

U.S. Pat. No. 4,857,078, to Watler, mentions that, in natural gas liquids recovery, streams that are enriched in hydrogen can be produced as retentate by a rubbery membrane.

U.S. Pat. No. 4,772,295, to Nippon Kokan Kabushiki Kaisha, discloses a process using a membrane loop to recirculate hydrocarbon enriched vapors to an absorption column.

Treatment schemes for gas mixtures that include light olefin components and hydrogen are known. U.S. Pat. No. 5,634,354, to Air Products, discloses recovery of hydrogen and olefins from gas streams containing mixtures of the same. The recovery process uses a membrane separation system to remove hydrogen from the gas mixture, followed by low-temperature condensation of the hydrocarbons. The membrane used to perform the separation is either a polymeric membrane selective for hydrogen over hydrocarbons or a carbon adsorbent membrane selective for hydrocarbons over hydrogen. Separation of refinery waste gases by means of adsorbent membrane/PSA hybrid systems is described in some detail in reports by M. Anand and K. A. Ludwig to the U.S. Department of Energy ("Novel Selective Surface Flow Membranes for the Recovery of Hydrogen from Waste Gas Streams", Phase I (1995) and Phase II (1996) Final Reports under contract number DE-FC04-93AL94461). Separation of such gases, also containing olefins, is discussed in materials distributed at a U.S. Department of Energy, Office of Industrial Technology, exhibit in Washington, D.C. ("Scale-Up of Selective Surface Flow Membrane for Gas Separation", T. Nahieri et al., Air Products and Chemicals, 1996). U.S. Pat. No. 5,082,481, to Lummus Crest, describes removal of carbon dioxide, hydrogen and water vapor from a cracking effluent light gas stream, the hydrogen separation being accomplished by a hydrogen-selective membrane. U.S. Pat. No. 5,452,581, to Dinh et al., describes the use of a hydrogen-selective membrane as part of the ethylene recovery system for treating effluent from an ethylene manufacturing facility. The membrane is used to remove hydrogen to raise the hydrocarbon dewpoint of the gas, thereby facilitating olefin recovery.

SUMMARY OF THE INVENTION

The invention is a process for improved catalytic cracking, and specifically for improved recovery of olefins, LPG and/or and hydrogen from catalytic crackers. The new process includes a membrane separation treatment, which is preferably used to treat overhead gases from the absorption section of the vapor recovery section of the plant.

In a basic aspect, the invention comprises the following steps:

(a) cracking a hydrocarbon feedstock;

(b) fractionating the hydrocarbon product of step (a) to produce at least one liquid stream and an overhead vapor stream;

(c) cooling at least a part of the overhead vapor stream, thereby producing an overhead liquid stream and a wet gas stream;

(d) compressing at least a part of the wet gas stream;

(e) separating the compressed wet gas stream into a hydrocarbon liquid portion and a vapor portion;

(f) passing at least a part of the vapor portion through at least one absorption step to absorb $C_{3+}$ hydrocarbon components, thereby producing a lighter vapor portion;

(g) passing at least a part of the lighter vapor portion as a feed gas across the feed side of a polymeric membrane having a feed side and a permeate side and being selectively permeable to $C_{2+}$ hydrocarbons over hydrogen;

(h) withdrawing from the permeate side a permeate stream enriched in $C_{2+}$ hydrocarbons compared with the feed gas;

(i) withdrawing from the feed side a residue stream enriched in hydrogen compared with the feed gas.

As it relates to treatment of overhead gases from the absorption section of the unsaturated gas treatment section of the plant, the invention comprises the following steps:

(a) withdrawing the overhead gas stream from the column;

(b) passing the gas stream as a feed gas across the feed side of a polymeric membrane having a feed side and a permeate side and being selectively permeable to $C_{2+}$ hydrocarbons over hydrogen;

(c) withdrawing from the permeate side a permeate stream enriched in $C_{2+}$ hydrocarbons compared with the feed gas;

(d) withdrawing from the feed side a residue stream enriched in hydrogen compared with the feed gas;

(e) passing the permeate stream to a further treatment step to produce at least one hydrocarbon product.

Preferred embodiments of the invention include compressing and cooling the absorption column overhead stream before it passes to the membrane separation unit. In this case, the compression/cooling steps cause condensation of some of the heavier components in the stream, enabling an LPG stream to be withdrawn at this point. The lighter uncondensed fraction passes on to the membrane separation step.

As an alternative, it is possible to use the membrane separation unit to replace, rather than supplement, the absorption section of the plant. Embodiments of this type include the following steps:

(a) cracking a hydrocarbon feedstock;

(b) fractionating the hydrocarbon product of step (a) to produce at least one liquid stream and an overhead vapor stream;

(c) cooling at least a part of the overhead vapor stream, thereby producing an overhead liquid stream and a wet gas stream;

(d) compressing at least a part of the wet gas stream;

(e) separating the compressed wet gas stream into a hydrocarbon liquid portion and a vapor portion;

(f) passing at least a part of the vapor portion as a feed gas across the feed side of a polymeric membrane having a feed side and a permeate side and being selectively permeable to $C_{2+}$ hydrocarbons over hydrogen;

(g) withdrawing from the permeate side a permeate stream enriched in $C_{2+}$ hydrocarbons compared with the feed gas;

(h) withdrawing from the feed side a residue stream enriched in hydrogen compared with the feed gas;

(i) passing the permeate stream to a further treatment step to produce at least one hydrocarbon product.

In another aspect, the invention is a catalytic cracking apparatus, including cracking, fractionation, gasoline recovery and gas treatment sections.

The invention has an important advantage over other processes including polymeric membrane separation treatment that have been used in the refining industry in the past: the membranes are hydrogen-rejecting. That is, hydrocarbons permeate the membrane preferentially, leaving a residue stream on the feed side that is concentrated in the slower-permeating hydrogen. This greatly facilitates further treatment and use of the hydrogen stream. For example, the invention can be used to produce a high purity (99%+) hydrogen stream by including a pressure swing adsorption (PSA) unit to upgrade the hydrogen-enriched residue stream from the membrane. Since the hydrogen-enriched stream from the membrane remains at the relatively high pressure of the feed side, it may be passed to the adsorption step without the recompression that would be needed if the hydrogen were in the permeate stream.

Polymeric materials are used for the membranes. This renders the membranes easy and inexpensive to prepare, and to house in modules, by conventional industrial techniques, unlike other types of hydrogen-rejecting membranes, such as finely microporous inorganic membranes, including adsorbent carbon membranes, pyrolysed carbon membranes and ceramic membranes, which are very difficult and costly to fabricate in industrially useful quantities.

A particularly important advantage is that the preferred membranes used in the present invention permeate hydrocarbons, hydrogen sulfide, carbon dioxide, ammonia and water vapor preferentially over hydrogen, and are capable of withstanding exposure to these materials even in high concentrations. This contrasts with cellulose acetate and like membranes, which must be protected from exposure to heavy hydrocarbons and water. If liquid water or $C_{3+}$ hydrocarbons condense on the surface of such membranes, as can happen as described above, the membranes can suffer catastrophic failure. On the other hand, the membranes used in the invention preferentially and rapidly pass these components, so they do not build up on the feed side. Also, unlike other types of hydrogen-rejecting membranes, such as adsorbent carbon membranes, the presence of a heavier hydrocarbon component does not have a significant negative impact on the permeation of a lighter component. For example, the presence of small amounts of $C_{5+}$ hydrocarbons will not impede the ability of the membrane to remove $C_{3+}$ hydrocarbons. Thus, the membranes can handle a diversity of stream types including, for example, gases containing hydrogen sulfide and comparatively heavy hydrocarbons, such as $C_{6+}$ hydrocarbons. This is very useful when handling gas stream from catalytic crackers, which are often relatively "dirty"; that is, they contain multiple contaminants of the types mentioned.

All of the unit treatment steps of the invention may be carried out in one or multiple stages in diverse arrangements. For example, wet gas compression is frequently performed by multiple compressors, and the absorption section usually contains primary and secondary absorbers. The membrane separation step also may take the form of a single step or of multiple sub-steps, depending on the feed composition, membrane properties and desired results.

Additional treatment steps may be included in the process train as appropriate. For example, the raw gasoline liquids recovered from the main fractionation column overhead are usually passed through debutanizers and the like to remove lighter components, and the side and bottom streams from the main column are typically subjected to various purification and polishing operations.

It is to be understood that the above summary and the following detailed description are intended to explain and illustrate the invention without restricting its scope.

DETAILED DESCRIPTION OF THE INVENTION

The terms gas and vapor are used interchangeably herein.

The term $C_{2+}$ hydrocarbon means a hydrocarbon having at least two carbon atoms; the term $C_{3+}$ hydrocarbon means a hydrocarbon having at least three carbon atoms; and so on.

The term $C_{2-}$ hydrocarbon means a hydrocarbon having no more than two carbon atoms; the term $C_{3-}$ hydrocarbon means a hydrocarbon having no more than three carbon atoms; and so on.

The term light hydrocarbon means a hydrocarbon molecule having no more than about six carbon atoms.

The term lighter hydrocarbons means $C_1$ or $C_2$ hydrocarbons.

The term heavier hydrocarbons means $C_{3+}$ hydrocarbons.

The terms two-step and multistep as used herein with regard to a membrane separation unit mean an arrangement of membrane modules or banks of membrane modules connected together such that the residue stream from one module or bank of modules becomes the feedstream for the next.

The terms two-stage and multistage as used herein with regard to a membrane separation unit mean an arrangement of membrane modules or banks of membrane modules connected together such that the permeate stream from one module or bank of modules becomes the feedstream for the next.

The term membrane array means a set of membrane modules or banks of modules connected in a multistep arrangement, multistage arrangement, or mixtures or combinations of these.

The term product residue stream means the residue stream exiting a membrane array when the membrane separation process is complete. This stream may be derived from one membrane bank, or may be the pooled residue streams from several membrane banks.

The term product permeate stream means the permeate stream exiting a membrane array when the membrane separation process is complete. This stream may be derived from one membrane bank, or may be the pooled permeate streams from several membrane banks.

Percentages herein are by volume unless otherwise stated.

The invention is a process for improved catalytic cracking, and specifically for improved recovery of olefins, LPG, gasoline and/or hydrogen from catalytic crackers. The new process includes a membrane separation treatment, which is preferably used to treat overhead gases from the absorption section of the vapor recovery section of the plant.

Figure 1:
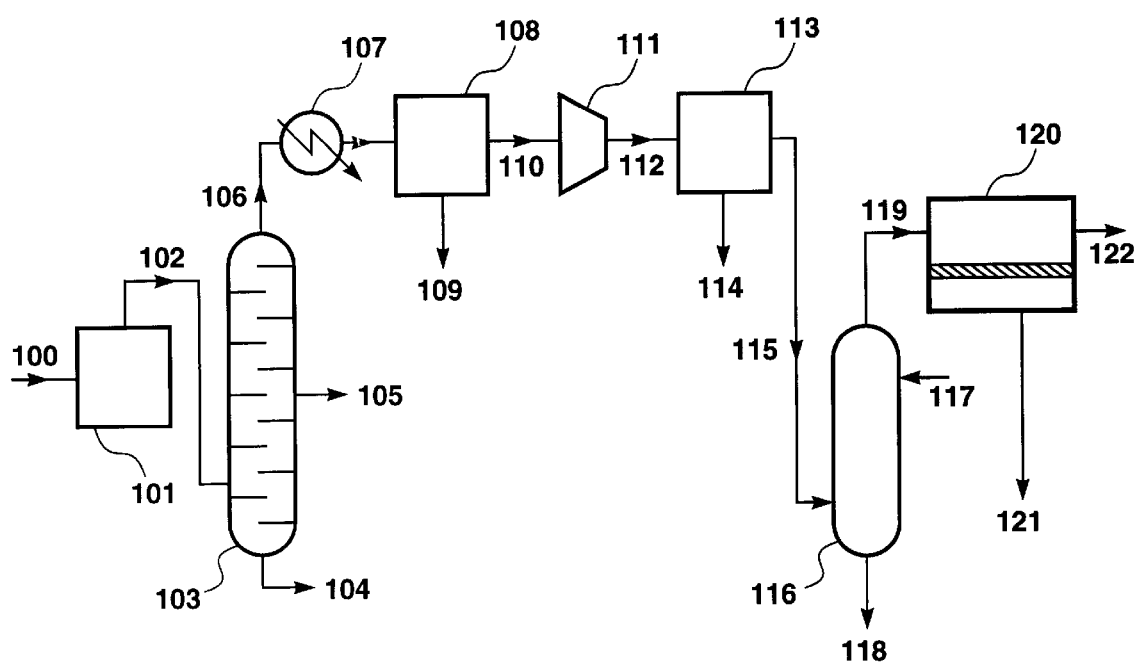
FIG. 1 is a schematic drawing of a basic embodiment of the invention.

The invention in a basic aspect is shown schematically in FIG. 1. It will be appreciated by those of skill in the art that this, and the other figures described below, are very simple schematic diagrams. These are intended to make clear the essential elements of the invention, and in particular the manner in which the membrane separation step is included. Those of skill in the art will appreciate that a catalytic cracking process train will usually include many additional components of a standard type, such as heaters, chillers, condensers, pumps, blowers, other types of separation and/or fractionation equipment, valves, switches, controllers, pressure-, temperature-, level- and flow-measuring devices and the like.

Referring now to FIG. 1, box 101 represents the main reactor section of the catalytic cracker, also referred to as the converter. Catalytic crackers are well known in the art and do not require any lengthy description herein. A reference that provides discussion of design and operation of modern FCC units is Chapter 3 of "Handbook of Petroleum Refining Processes" Second Edition, R. A. Meyers (Ed), McGraw Hill, 1997. The reactor is normally made up of a riser, often called the riser-reactor, where the catalytic cracking reactions take place, a disengagement section above the riser where the catalyst and crackate are separated, a stripping section to remove entrained hydrocarbons from the catalyst, and a regenerator, where the catalyst is decoked for reuse.

A mixture of the hydrocarbon feedstock and steam, generally indicated as stream 100, is injected into the riser. This stream is preheated to ensure that it is at the correct temperature when it enters the riser. Hot catalyst is also passed upward through the riser. The temperature in the riser section has a substantial influence on which reactions will take place, how far and how fast they will proceed, and what product mix will result. Typically, riser temperatures are in the range 450–575° C., most commonly 500–550° C. When the hot catalyst and the feedstock oil mix together, cracking reactions begin immediately. Over a matter of seconds, cracked products are formed and carried up the riser into the catalyst separation section. As the reactions occur, the catalyst becomes coated with coke, as a result of hydrocarbon condensation reactions. If the catalyst and feedstock are not separated rapidly, the reactions proceed until the product is gas rather than gasoline. The catalyst/hydrocarbons mix rises into the reactor disengagement section, which preferably contains staged primary and secondary cyclone separators to quickly separate the hydrocarbon and catalyst. The separated catalyst drops under gravity into the stripping section, where steam is injected to remove remaining entrained hydrocarbons. Finally, the catalyst passes into the regenerator section of the reactor. Here, the catalyst is regenerated under carefully controlled conditions by passing a heated air stream into the regenerator. This burns off the surface coke and restores the catalyst to working condition. The exhaust gases from the regenerator, typically containing carbon dioxide, carbon monoxide, $SO_x$ and $NO_x$ are very hot, such as above 700° C., and are used for heat exchange against incoming streams before being discharged. The regenerated catalyst is passed back to the bottom of the riser section and the cycle begins again.

The reactor can be adjusted to run in various modes. Three important modes are maximum gasoline, maximum light cycle oil (LCO) and maximum light olefin. Maximum gasoline mode demands a relatively high catalyst:feedstock ratio, a high-activity catalyst, and a short reaction time. Intermediate riser temperatures are used. Care must be taken to minimize the secondary reactions that break down the gasoline into light gases after it exits the riser section. FCC units are often run in this mode in the summer, when demand for gasoline is high and demand for heating oils is low. In contrast, maximum LCO mode is often used in the winter to increase fuel oil production. This mode demands lower catalyst activity and lower catalyst:feedstock ratio. Since the feedstock conversion is lower than in maximum gasoline mode, the heavy bottom fractions are often recirculated to the riser. As has been mentioned above, gases form when the cracking reactions continue beyond gasoline formation. If light olefins are a preferred product, their formation can be enhanced by operating at high riser temperatures, such as above 540° C., and by using catalysts that favor these reactions.

The product hydrocarbon vapors, stream 102, leave through the top of the reactor and pass to the main distillation column, 103, for fractionation. Numerous products can be retrieved from the raw crackate. The fractionation column is run to produce an overhead stream, 106, that contains mostly $C_5$ and lighter hydrocarbons. Because of the conditions under which the cracking takes place, this fraction contains substantial amounts of unsaturated hydrocarbons, particularly ethylene and propylene. The bottom fraction, 104, from the column consists of a heavy slurry of uncracked materials. This fraction can be clarified, then sold as heavy fuel, or for manufacture of specialized products, such as electrodes. Several side streams, indicated in the aggregate as stream 105, can be taken from the column. These generally include naphtha, light cycle oil (LCO) and heavy cycle oil (HCO) and may be desulfurized, further fractionated or treated as otherwise required, and used for diesel fuel, home heating oils and heavy fuel oils, for example.

The overhead stream from the column is cooled in cooler 107. Typically, but not necessarily, air cooling is used, supplemented by additional trim cooling if needed. The cooled stream is passed into receiver or accumulator, 108, where phase separation into a condensate of raw, unstabilized gasoline and an uncondensed vapor, known as wet gas, takes place. As described below, part of the condensate stream is often used downstream in the absorber section, then returned to the separator. The net unstabilized gasoline stream, 109, is withdrawn from the accumulator, and is passed to a debutanizer column and/or other fractionation or treatment to yield the stabilized gasoline product. Condensation also usually results in formation of a small sour water stream, not shown, which is withdrawn as a separate phase from the accumulator vessel. The wet gas stream now contains hydrogen, $C_1-C_4$ hydrocarbons, small amounts of heavier hydrocarbons, water vapor, and other light contaminants.

The wet gas stream, 110, is drawn out of the separator and passed through wet gas compression step, 111. This step can be carried out in one or multiple compression stages. Commonly, but not necessarily, compression is performed with a train comprising two stages of centrifugal compressors, with one or more interstage receivers to collect the additional raw gasoline and sour water that is condensed here. The compression step also normally includes aftercooling by air cooling. Box 111 is intended to indicate any convenient type of wet gas compression step consistent with the general teachings given above. The liquid and gas phases that are formed by compression are subjected to phase separation, 113, to yield unstabilized gasoline stream, 114, and vapor stream 115. A sour water stream, not shown, is also commonly withdrawn here.

Vapor stream 115 passes to the absorption section, 116, of the gas treatment plant. Here the vapor is brought into contact with a hydrocarbon liquid and heavier hydrocarbon components remaining in the vapor partition into the liquid. As with the compression step, the absorption step may be carried out by any convenient technique known in the art. Common and preferred practice is to pass the vapor through a primary absorber and a secondary absorber in series. The absorbers are preferably trayed or packed columns, into which the vapor is introduced at the bottom. The vapor passes up the column flowing countercurrent to the hydrocarbon liquid stream, which is introduced at the top of the column, as stream 117. In the refinery environment, a variety of hydrocarbon liquids are available for use as sorbents. Many prior art catalytic crackers operate using unstabilized gasoline as sorbent in the primary absorber and a naphtha cut from the main fractionation column as sorbent in the secondary absorber. With reference to FIG. 1, therefore, it is preferred that at least a part of stream 109 and optionally stream 114 comprise the liquid sorbent feed to the primary column. Gasoline fractions recovered downstream may also form part of the sorbent liquid for this column. The net effect of the contact is to transfer $C_{3+}$ hydrocarbons to the liquid phase. Again with reference to the figure, a lean fraction from stream 105, such as naphtha or light cycle oil, comprises the preferred sorbent for the secondary absorber, often called the sponge absorber. This column absorbs most of the remaining $C_{5+}$ hydrocarbon components, plus some lighter components.

The rich liquids formed in the absorption step, indicated generally as stream 118 in FIG. 1, are withdrawn from the column or columns and sent to appropriate destinations. Those of skill in the art will appreciate that in the typical situation where a primary absorber column and a sponge absorber column are used, each column will produce its own liquid bottom stream. Preferably, the sponge oil is passed back into the main fractionation column. The bottom stream from the primary absorber is usually passed back to the phase separator that follows the wet gas compressor.

The lighter gas, stream 119, remaining after the absorption section usually contains 15–30% hydrogen and 30–60% $C_1/C_2$ hydrocarbons. Thus, although the gas is substantially a methane/hydrogen mix, it may still contain 10% or more of $C_{3+}$ hydrocarbons and a significant light olefin component. It also carries the remains of contaminants, particularly hydrogen sulfide, that have not partitioned into other streams along the treatment train. In prior art catalytic cracker trains, this gas must often be scrubbed to remove acid gas before being passed to the fuel gas line. Typically, scrubbing is done by passing the gas through an amine solution, as is well known in the art One of the new aspects and particular advantages of the invention is that membranes that are selective for hydrogen sulfide over hydrogen are used to treat the overhead vapors from the absorber. Thus, since treatment to remove hydrogen sulfide is no longer necessary, absorber overhead stream 119 is shown in FIG. 1 as being passed without amine treatment to membrane separation step, 120. If it is desired to capture the acid gases before the membrane unit, for example because of specifications for the permeate stream content, an amine scrubbing unit or the like may optionally be included upstream of unit 120.

The membrane unit contains a membrane that exhibits a substantially different permeability for hydrocarbons than for hydrogen. The permeability of a gas or vapor through a membrane is a product of the diffusion coefficient, D, and the Henry's law sorption coefficient, k. D is a measure of the permeant's mobility in the polymer; k is a measure of the permeant's sorption into the polymer. The diffusion coefficient tends to decrease as the molecular size of the permeant increases, because large molecules interact with more segments of the polymer chains and are thus less mobile. The sorption coefficient depends, amongst other factors, on the condensability of the gas.

Depending on the nature of the polymer, either the diffusion or the sorption component of the permeability may dominate. In rigid, glassy polymer materials, the diffusion coefficient tends to be the controlling factor and the ability of molecules to permeate is very size dependent. As a result, glassy membranes tend to permeate small, low-boiling molecules, such as hydrogen and methane, faster than larger, more condensable molecules, such as $C_{2+}$ organic molecules. For rubbery or elastomeric polymers, the difference in size is much less critical, because the polymer chains can be flexed, and sorption effects generally dominate the permeability. Elastomeric materials, therefore, tend to permeate large, condensable molecules faster than small, low-boiling molecules. Thus, most rubbery materials are selective in favor of all $C_{3+}$ hydrocarbons over hydrogen. However, for the smallest, least condensable hydrocarbons, methane in particular, even rubbery polymers tend to be selective in favor of hydrogen, because of the relative ease with which the hydrogen molecule can diffuse through most materials. For example, neoprene rubber has a selectivity for hydrogen over methane of about 4, natural rubber a selectivity for hydrogen over methane of about 1.6, and Kraton, a commercial polystyrene-butadiene copolymer, has a selectivity for hydrogen over methane of about 2.

Any rubbery material that is selective for $C_{2+}$ hydrocarbons over hydrogen will provide selective purging of these components and can be used in the invention. Examples of polymers that can be used to make such elastomeric membranes, include, but are not limited to, nitrile rubber, neoprene, polydimethylsiloxane (silicone rubber), chlorosulfonated polyethylene, polysilicone-carbonate copolymers, fluoroelastomers, plasticized polyvinylchloride, polyurethane, cis-polybutadiene, cis-polyisoprene, poly(butene-1), polystyrene-butadiene copolymers, styrene/butadiene/styrene block copolymers, styrene/ethylene/butylene block copolymers, and thermoplastic polyolefin elastomers.

However, the most preferred membrane differs from other membranes used in the past in refinery and petrochemical processing applications in that it is more permeable to all hydrocarbons, including methane, than it is to hydrogen. In other words, unlike almost all other membranes, rubbery or glassy, the membrane is methane/hydrogen selective, that is, hydrogen rejecting, so that the permeate stream is hydrogen depleted and the residue stream is hydrogen enriched, compared with the membrane feed stream. To applicants' knowledge, among the polymeric membranes that perform gas separation based on the solution/diffusion mechanism, silicone rubber is the only material that is selective in favor of methane over hydrogen. As will now be appreciated by those of skill in the art, at least some of the benefits that accrue from the invention derive from the use of a membrane that is both polymeric and hydrogen rejecting. Thus, any polymeric membrane that is found to have a methane/hydrogen selectivity greater than 1 can be used for the processes disclosed herein and is within the scope of the invention. For example, other materials that might perhaps be found by appropriate experimentation to be methane/hydrogen selective include other polysiloxanes. Another class of polymer materials that has at least a few members that should be methane/hydrogen selective, at least in multicomponent mixtures including other more condensable hydrocarbons, is the superglassy polymers, such as poly(1-trimethylsilyl-1-propyne) [PTMSP] and poly(4-methyl-2-pentyne) [PMP]. These differ from other polymeric membranes in that they do not separate component gases by solution/diffusion through the polymer. Rather, gas transport is believed to occur based on preferential sorption and diffusion on the surfaces of interconnected, comparatively long-lasting free-volume elements. Membranes and modules made from these polymers are less well developed to date; this class of materials is, therefore, less preferred than silicone rubber.

A third type of membrane that may be used if hydrogen sulfide is of concern is one in which the selective layer is a polyamide-polyether block copolymers having the general formula

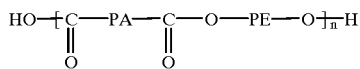

where PA is a polyamide segment, PE is a polyether segment and n is a positive integer. Such polymers are available commercially as Pebax® from Atochem Inc., Glen Rock, N.J. or as Vestamid® from Nuodex Inc., Piscataway, N.J. These types of materials are described in detail in U.S. Pat. No. 4,963,165, for example. Such membranes will remove hydrogen sulfide with a very high selectivity, such as 20 or more, for hydrogen sulfide over hydrogen. They are however selective in favor of hydrogen over methane, with a selectivity of about 1 to 2, depending on grade, so are not preferred where it is desired to produce a high hydrogen concentration stream as the residue stream.

The gas stream enters the membrane separation step and flows across the surface of the hydrocarbon-selective membranes, producing residue stream 122 and permeate stream 121.

The membranes may take any convenient form known in the art. The preferred form is a composite membrane including a microporous support layer for mechanical strength and a silicone rubber coating layer that is responsible for the separation properties. Additional layers may be included in the structure as desired, such as to provide strength, protect the selective layer from abrasion, and so on.

The membranes may be manufactured as flat sheets or as fibers and housed in any convenient module form, including spiral-wound modules, plate-and-frame modules and potted hollow-fiber modules. The making of all these types of membranes and modules is well known in the art. Flat-sheet membranes in spiral-wound modules are our most preferred choice. Since conventional polymeric materials are used for the membranes, they are relatively easy and inexpensive to prepare and to house in modules, compared with other types of membranes that might be used as hydrogen-rejecting membranes, such as finely microporous inorganic membranes, including adsorbent carbon membranes, pyrolysed carbon membranes and ceramic membranes.

To achieve a high flux of the preferentially permeating hydrocarbons, the selective layer responsible for the separation properties should be thin, preferably, but not necessarily, no more than 30 μm thick, more preferably no more than 20 μm thick, and most preferably no more than 5 μm thick. If superglassy materials are used, their permeabilities are so high that thicker membranes are possible. A benefit of using silicone rubber or superglassy membranes is that they provide much higher transmembrane fluxes than conventional glassy membranes. For example, the permeability of silicone rubber to methane is 800 Barrer, compared with a permeability of only less than 10 Barrer for 6FDA polyimide or cellulose acetate.

A driving force for transmembrane permeation is provided by a pressure difference between the feed and permeate sides of the membrane. The overhead stream as supplied from the absorbers is normally at a pressure of a few atmospheres, for example about 75 psia. Maintaining the permeate side of the membrane system at atmospheric pressure thus typically provides a pressure ratio of about 5 between the feed and permeate sides. Based on the selectivities provided by, for example, silicone rubber membranes for hydrocarbons over hydrogen, this pressure ratio is adequate to provide good separation for a range of stream compositions. However, a compressor may optionally be included in line 119 to boost the pressure on the feed side of the system. If compression is used, pressures of no more than 500 psia, and preferably about 200 psia or 300 psia are preferred. The residue stream remains at or close to the pressure of the feed stream, subject only to a slight pressure drop along the feed surface of the membrane modules.

Depending on the composition of the membrane feed stream 119, a single-stage membrane separation operation may be adequate to produce a permeate stream with an acceptably high hydrocarbon content and low hydrogen content. If the permeate stream requires further separation, it may be passed to a second bank of modules for a second-stage treatment. If the second permeate stream requires further purification, it may be passed to a third bank of modules for a third processing step, and so on. Likewise, if the residue stream requires further contaminant removal, it may be passed to a second bank of modules for a second-step treatment, and so on. Such multistage or multistep processes, and variants thereof, will be familiar to those of skill in the art, who will appreciate that the membrane separation step may be configured in many possible ways, including single-stage, multistage, multistep, or more complicated arrays of two or more units in series or cascade arrangements. Representative embodiments of a few of such arrangements are given in copending Ser. No. 09/083,660 entitled "Selective Purge for Reactor Recycle Loop", incorporated herein by reference in its entirety. Examples of such arrangements are also described in U.S. Pat. No. 5,256,295.

The membrane separation step is used to make a hydrogen/hydrocarbon separation. By selectively removing the non-hydrogen components, the process results in a membrane residue stream, 122, that is enriched in hydrogen content compared with stream 119. Of course, if desired, the membrane separation unit can be configured and operated to provide a residue stream that has a significantly higher hydrogen concentration compared with the feed, such as 90 vol %, 95 vol % or more, subject only to the presence of any other slow-permeating component, such as nitrogen, in the feed. This can be accomplished by increasing the stage-cut of the membrane separation step, that is, the ratio of permeate flow to feed flow, to the point that little of anything except hydrogen is left in the residue stream. As the stage-cut is raised, however, more hydrogen is lost into the permeate stream. This can be clearly seen by considering that, in the limit, if the stage-cut were allowed to go to 100%, all of the gas present in the feed would pass to the permeate side of the membrane and no separation would take place.

Conversely, if a very low stage-cut is used, a permeate stream with a very high concentration of $C_{3+}$ hydrocarbons, including propylene, can be obtained, but a significant fraction of the heavier hydrocarbons will remain in the residue stream. Those of skill in the art will appreciate that the membrane area and membrane separation step operating conditions can be chosen depending on whether the composition of the permeate or the residue stream is of more importance. For example, the concentration of $C_{3+}$ hydrocarbons might be raised from 20 vol % in the feed to about 50 vol % in the permeate. Correspondingly, the hydrogen content might be diminished from 20 vol % in the feed to about 5 vol % in the permeate. Alternatively, the hydrogen concentration might be raised from 20 vol % in the feed to 40 vol % in the residue, with a corresponding drop in $C_{3+}$ hydrocarbons from 45 vol % in the feed to 30 vol % in the residue. Illustrations of the effect of varying the stage-cut are given in the Examples section below. As a general guideline, it is preferred to operate at a stage-cut between 20% and 80%, and more preferably between 30% and 70%, or between 40% and 60%. If hydrogen sulfide removal is of more interest that removing high levels of hydrocarbons, membranes with relatively high selectivity for hydrogen sulfide over hydrogen, such as polyamide-polyether block copolymer membranes, can be used and a lower stage-cut, such as below 40%, may be preferred.

Permeate stream, 121, is withdrawn from the membrane separation step. If the membrane separation step is carried out principally to increase hydrocarbon recovery from the cracker, this stream will typically contain as much as 50–60% or more $C_{3+}$ hydrocarbons, as much as 30–40% propylene, and as much as 10–20% ethylene. The combined methane, ethane and hydrogen content in this case is typically below 30–40%. This stream may simply be condensed to form LPG, but, as will be appreciated by those of skill in the art, is also very suitable for further separation, by distillation or otherwise, such as to recover olefins. Representative, but non-limiting, destinations to which this stream can be passed include the main fractionation column and other distillation columns, such as downstream debutanizer and depropanizer columns, $C_3$ splitters for propylene recovery and $C_2$ splitters for ethylene recovery. If the process is carried out primarily to upgrade the hydrogen content of the absorber overhead gas, the permeate stream may have lower hydrocarbon concentrations than those mentioned and may be sent to the fuel gas line.

Residue stream, 122, is withdrawn from the membrane separation step. This stream typically contains 30–50% hydrogen if a single-step membrane configuration is used, and about 60% or more hydrogen if a multistep arrangement, such as the ones described in copending Ser. No. 09/083,660 entitled "Selective Purge for Reactor Recycle Loop", for example FIG. 6 and Examples 10–15, is used. This stream is preferably used as a hydrogen source for hydrogen consuming processes in the refinery, as is or after additional treatment. If a higher hydrogen concentration in the stream is required, it may be passed to an additional treatment step. Discussion of these additional treatments is given below, with respect to FIGS. 2 and 5, and the considerations and preferences given there with regard to additional treatments apply equally to the embodiments of FIG. 1. If the process is carried out primarily to increase the hydrocarbon concentration of the absorber overhead gas, the residue stream may have lower hydrogen concentrations than those mentioned and may be sent to the fuel gas line.

Figure 2:
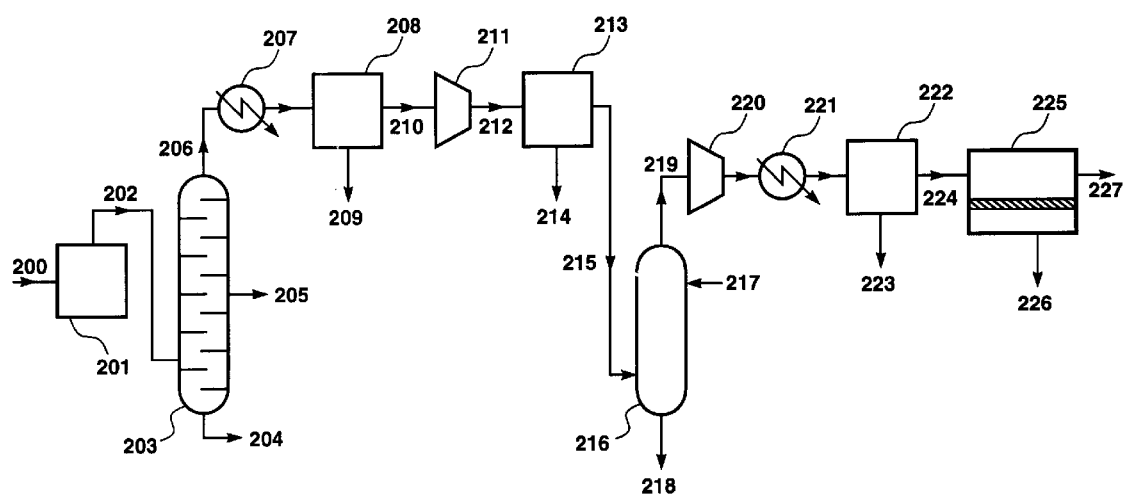
FIG. 2 is a schematic drawing of an embodiment of the invention including a condensation step before the membrane separation step.

If the absorber overhead stream is compressed before passing to the membrane separation step, a particularly preferred embodiment is that shown in FIG. 2. All of the considerations, preferences and other features discussed above with respect to the embodiment of FIG. 1 apply also to the embodiment of FIG. 2, except as explicitly described otherwise. Referring now to FIG. 2, box 201 represents the main reactor section or converter. The hydrocarbon feedstock stream, 200, enters the reactor, where it is cracked to produce product stream 202, which passes to the main distillation column, 203, for fractionation. The fractionation column separates the raw crackate into gasoline/gas overhead stream, 206, bottom slurry oil, 204, and side cuts 205.

The overhead stream from the column is cooled in cooler 207 and passed into separator 208. Unstabilized gasoline stream, 209, is withdrawn and passed for downstream treatment. The wet gas stream, 210, is compressed in wet gas compression step, 211. The liquid and gas phases that are formed by compression are subjected to phase separation, 213, to yield unstabilized gasoline stream, 214, and vapor stream 215.

Vapor stream 215 passes to absorption section 216. Hydrocarbon sorbent, 217, also enters the section. As with the earlier described embodiment, use of two absorbers in series, using first the unstabilized gasoline, and then a lean sponge oil, to sorb heavier hydrocarbons is preferred. The loaded sorbent streams exit the section as indicated by line 218, and are passed to destinations as described for FIG. 1.

The lighter gas, stream 219, remaining after the absorption section optionally passes through an acid gas removal step, not shown. The stream enters compression step, 220. This step may be carried out using one or multiple compression stages, as convenient depending on the final pressure that is to be reached. In general, as explained above, very high pressures are not required and do not significantly improve the subsequent membrane separation. It is preferred to raise the stream to be a pressure no higher than 500 psia, more preferably no more than about 300 psia, or lower such as 200 psia. After leaving the compressor, the stream is cooled by cooler 221. The compression and cooling results in condensation of a heavier hydrocarbon LPG phase, 223, which is separated from the remaining gas, 224, in phase separator, 222.

Obviously the amount of LPG liquid produced here is a function of the pressure and temperature conditions, and those of skill in the art will understand that a trade-off is made between liquids recovery and compression and cooling costs. We prefer to use one or combinations of air cooling, water cooling and heat exchange against other streams to reach the desired temperature. A benefit of preferential hydrocarbon permeation through the membranes is that the membrane thereby serves as an expansion device for a gas fraction that undergoes significant Joule-Thomson cooling, as described in U.S. Pat. No. 5,762,685. As a result, the membrane separation step can produce streams that are significantly colder, such as 10° C., 20° C. or more colder, than the membrane feed stream. These streams can be used to provide cooling for the condensation step. If air cooling, water cooling and/or heat exchange are used, the temperature of the cooled stream is above 0° C., such as 15° C. or 5° C. Less preferred, but optional, is to use external refrigeration to cool the stream to below 0° C., such as to −5° C. or −15° C. The lower the temperature, the more ethylene will be captured in the LPG stream.

Uncondensed stream, 224, passes into membrane separation step 225, containing membranes selective for at least the $C_{2+}$ hydrocarbons over hydrogen. All of the considerations, options and preferences described with respect to the membrane unit in FIG. 1 apply also to the embodiments of FIG. 2. As before, the membrane unit divides the stream into hydrogen-enriched stream 227 and hydrocarbon-enriched stream 226. This embodiment produces two hydrocarbon streams, 223 and 226. Each may be withdrawn separately and sent to a downstream destination appropriate to the composition and intended use.

Figure 4:
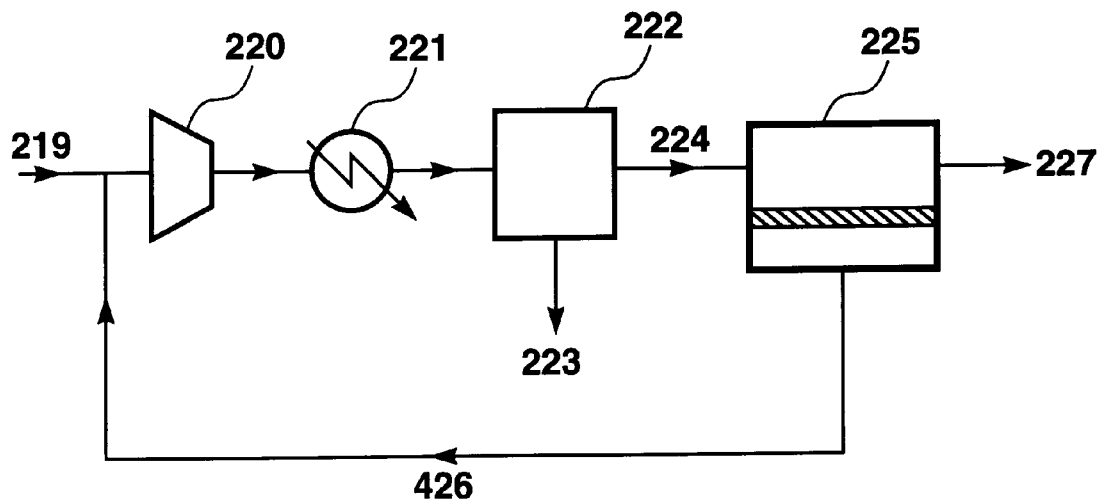
FIG. 4 is a schematic drawing showing an alternative embodiment of the membrane separation step, including recirculation of the membrane permeate stream to the compressor inlet.

An especially preferred arrangement, however, is to recirculate the permeate stream 226 to the inlet side of the compression stage. This arrangement is shown in FIG. 4, where like elements are numbered as in FIG. 2. Stream 426 is passed back and mixed with stream 219 on the suction side of compressor 220. Such embodiments may be used to build up the concentration of heavier components in stream 219 to facilitate condensation. Processes and systems of this type that integrate a condensation step and a membrane separation step are described, for example, in U.S. Pat. No. 5,199,962, incorporated herein by reference.

Figure 5:
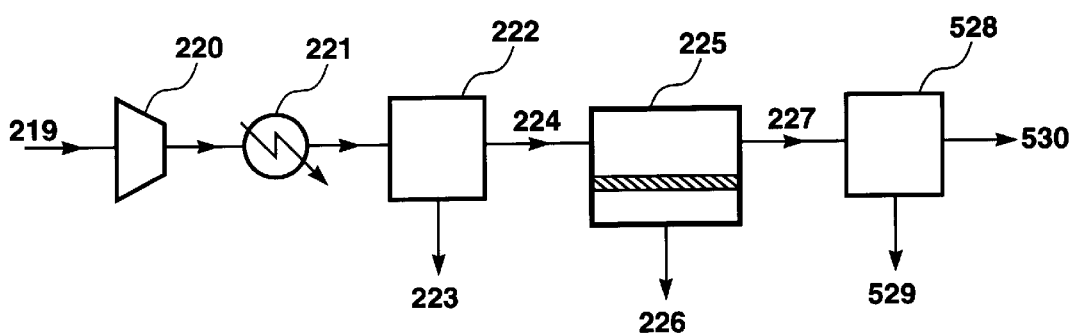
FIG. 5 is a schematic drawing showing an alternative embodiment of the membrane separation step, including additional treatment of the residue stream.

The residue stream is preferably used as a hydrogen source for hydrogen-consuming processes in the refinery, as is or after additional treatment. If a higher hydrogen concentration in the stream is required, it may be passed to an additional treatment step, of any convenient type, as shown in FIG. 5, where like elements are numbered as in FIG. 2. Membrane residue stream 227 is passed to treatment step 528, resulting in a hydrogen product stream 529, and a waste gas stream 530, which may be passed to the fuel gas line.

Preferred treatments for step 528 are membrane separation, this time using a hydrogen-selective membrane, and pressure swing adsorption (PSA). An advantage of using a hydrogen-rejecting membrane for step 225 is that the hydrogen-enriched stream remains on the high-pressure side of the membrane. This greatly facilitates further treatment. For example, if the further treatment is hydrogen-selective membrane separation, the residue stream, 227, can, optionally, be passed directly to this step without recompression. Likewise if the treatment is PSA, it is often possible to operate the system at the pressure of residue stream 227. In contrast, if a hydrogen-selective membrane were to be used for step 225, the permeate stream might be at only 10% or 20% the pressure of the feed, and would need substantial recompression before it could be subjected to further treatment. More details concerning combinations of a hydrocarbon-selective membrane unit with a hydrogen-selective membrane unit or with a PSA unit may be found in U.S. Pat. No. 6,011,192 entitled "Membrane-Based Conditioning For Adsorption System Feed Gases".

FIGS. 1 and 2 both embrace the aspect of the invention as it relates to treatment of the overhead stream from the absorption unit. Many of the teachings given herein with respect to operation of membrane separation systems in conjunction with absorption units can also be applied in a more general way to other situations where absorption columns producing overhead streams containing hydrocarbon vapors are found, such as other refinery units, petrochemical plants and the like.

In some catalytic cracking plants, the stream generated after wet gas compression, cooling and phase separation is treated not by lean oil absorption, but by cryogenic condensation. In such plants, retreated dry, clean gas is subjected to cryogenic distillation at temperatures of −60° C. or below, to produce a much lighter overhead stream. The systems can also be designed to upgrade the hydrogen concentration of the remaining gas to a level where it can be used directly in hydrogen-consuming processes. Although these plants offer better separation and recovery possibilities than those that rely on lean oil absorbers, the cost and complexity of operation are relatively high.

In a different aspect of our invention, it is possible to use the membrane separation unit to treat the gas from the wet gas compressor without first passing it through an absorption step, a cryogenic distillation step or extensive pretreatment steps.

Figure 3:
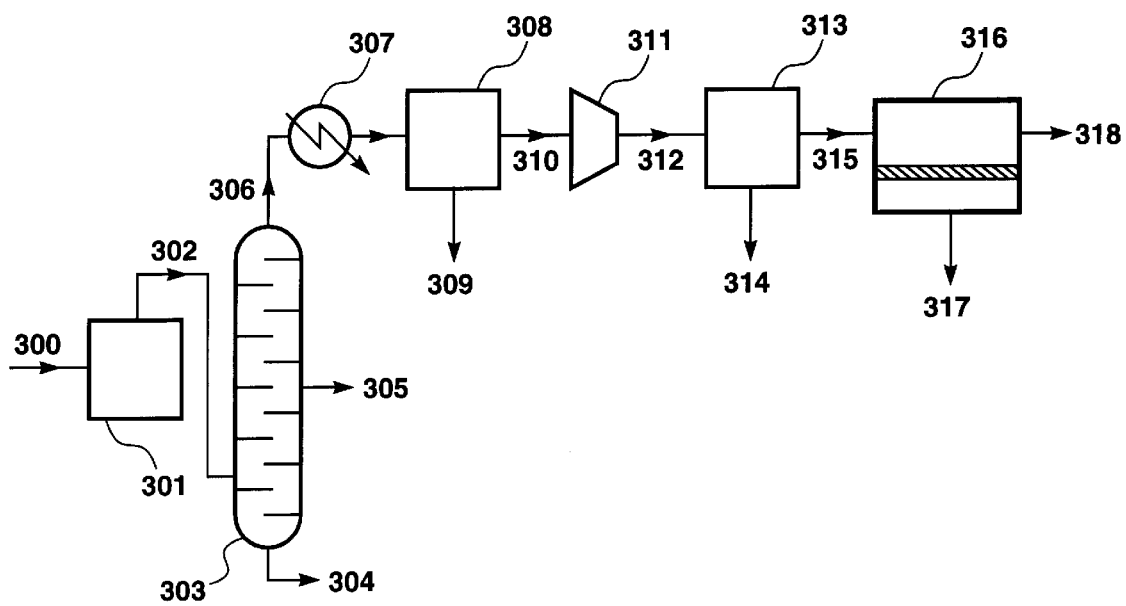
FIG. 3 is a schematic drawing of an embodiment of the invention in which gas from the wet gas compressor is passed to the membrane separation unit.

An embodiment of this type is shown in FIG. 3. Again, all of the considerations, preferences and other features discussed above with respect to the embodiment of FIG. 1 apply to the embodiment of FIG. 3, except as explicitly described otherwise. Referring now to FIG. 3, box 301 represents the main reactor section or converter. The hydrocarbon feedstock stream, 300, enters the reactor, where it is cracked to produce product stream 302, which passes to the main distillation column, 303, for fractionation. The fractionation column separates the raw crackate into gasoline/gas overhead stream, 306, bottom slurry oil, 304, and side cuts 305.

The overhead stream from the column is cooled in cooler 307 and passed into separator 308. Unstabilized gasoline stream, 309, is withdrawn and passed for downstream treatment. The wet gas stream, 310, is compressed in wet gas compression step, 311. The liquid and gas phases stream 312, that are formed by compression are subjected to phase separation, 313, to yield unstabilized gasoline stream, 314, and vapor stream 315.

In these embodiments, vapor stream 315 passes to membrane separation step 316. As with the previous embodiments, an acid gas removal step before the gas reaches the membrane separation unit is optional, but not required. Membrane separation step 316 contains membranes selective for at least the $C_{2+}$ hydrocarbons over hydrogen. All of the considerations, options and preferences described with respect to the membrane unit in FIG. 1 apply also to the embodiments of FIG. 3. As before, the membrane unit divides the stream into hydrogen-enriched stream 318 and hydrocarbon-enriched stream 317. The membrane process recovers the bulk of the LPG, including unsaturates, in the permeate stream, which can directed appropriately for production of liquid or to fractionation directly as a gas phase. A particular advantage of this arrangement is that the membrane process can operate at whatever temperature the wet gas stream is delivered, such as ambient or above, and requires little, if any, pretreatment compared to the cryogenic process. The membrane process can be followed by a pressure swing adsorption process for further hydrogen recovery. The off-gas from the PSA unit can then be added to the membrane permeate for LPG recovery.

The figures also show the elements of the apparatus of the invention in various embodiments. For example, referring again to FIG. 1, line 100 forms the feed stream inlet line carrying the raw hydrocarbon feedstock to the reactor 101. The reactor is capable of carrying out the type of catalytic cracking reactions described, and has an effluent outlet line, 102, through which fluid can pass, either directly as shown or via some intermediate treatment, such as cooling, to the fractionation column, 103. The fractionation column has liquid outlet lines, 104 and 105, and a vapor outlet line, 106. The vapor outlet line includes means, 107, for cooling the stream, such as an air cooler, heat exchanger of the like. The vapor outlet line is connected to an accumulator vessel, 108, adapted to provide phase separation of liquids and gases, and has a raw gasoline removal line, 109, and a gas outlet line, 110. The gas outlet line is connected to compressor, 111, which has a compressed gas outlet line, 112, that flows into receiver vessel, 113, adapted to provide phase separation between gases and liquids. This vessel has a gasoline outlet line, 114, and a gas outlet line, 115. The gas outlet line is connected to absorption unit, 116. The absorption unit is adapted to bring gases and liquids into fluid-transferring contact, and is equipped with sorbent inlet and outlet lines, 117 and 118 respectively, and an overhead gas outlet line, 119, which also forms feed inlet to membrane separation unit, 120. The membrane separation unit contains membranes that are selective in favor of $C_{2+}$ hydrocarbons over hydrogen, so as to produce a hydrocarbon-enriched permeate stream and a hydrocarbon-depleted, hydrogen-enriched residue stream. The membrane unit has a permeate side outlet line 121 and a residue, feed-side outlet line, 122

The invention is now further described by the following examples, which are intended to be illustrative of the invention, but are not intended to limit the scope or underlying principles in any way.

EXAMPLES 1–5

Effect of Increasing Stage-cut

EXAMPLE 1

A computer calculation was performed with a modeling program, ChemCad III (ChemStations, Inc., Houston, Tex.), to simulate the treatment of a typical overhead stream from the absorbers of a fluid catalytic cracker.

The stream was assumed to have a flow rate of 5 MMscfd and the following volume composition:

| | |
|---|---|
| Hydrogen | 20% |
| Methane | 15% |
| Ethane | 12.5% |
| Propane | 12.5% |
| n-Butane | 2.5% |
| n-Pentane | 2.5% |
| Ethylene | 10% |
| Propylene | 25% |

The treatment process was assumed to be carried out according to the membrane process design shown in FIG. 1.

Membrane pressure-normalized fluxes were assumed to be as follows, as are typical of a silicone rubber membrane:

| | |
|---|---|
| Hydrogen | $100 \times 10^{-6}$ cm$^3$(STP)/cm$^2$ · sec · cmHg |
| Methane | $140 \times 10^{-6}$ cm$^3$(STP)/cm$^2$ · sec · cmHg |
| Ethane | $350 \times 10^{-6}$ cm$^3$(STP)/cm$^2$ · sec · cmHg |
| Propane | $600 \times 10^{-6}$ cm$^3$(STP)/cm$^2$ · sec · cmHg |
| n-Butane | $1,400 \times 10^{-6}$ cm$^3$(STP)/cm$^2$ · sec · cmHg |
| n-Pentane | $2,000 \times 10^{-6}$ cm$^3$(STP)/cm$^2$ · sec · cmHg |
| Ethylene | $420 \times 10^{-6}$ cm$^3$(STP)/cm$^2$ · sec · cmHg |
| Propylene | $720 \times 10^{-6}$ cm$^3$(STP)/cm$^2$ · sec · cmHg |

The results of the calculations are shown in Table 1. The stream numbers correspond to FIG. 1.

TABLE 1

| Component/Parameter | Stream 119 | Stream 122 | Stream 121 |
|---|---|---|---|
| Flow rate (scfm) | 3,472 | 2,513 | 959 |
| Mass Flow Rate (lb/h) | 16,632 | 10,644 | 5,988 |
| Temperature (° C.) | 25 | 23 | 23 |
| Pressure (psia) | 75 | 75 | 15 |
| Component (mol %) | | | |
| Hydrogen | 20.0 | 25.0 | 6.9 |
| Methane | 15.0 | 18.1 | 6.9 |
| Ethane | 12.5 | 12.7 | 11.8 |
| Propane | 12.5 | 10.9 | 16.6 |
| n-Butane | 2.5 | 1.6 | 4.9 |
| n-Pentane | 2.5 | 1.4 | 5.5 |
| Ethylene | 10.0 | 9.7 | 10.7 |
| Propylene | 25.0 | 20.5 | 36.7 |

To perform this separation, 400 m$^2$ of membrane is needed, providing a stage-cut of 28%. The separation produces a permeate stream containing 47% olefins and over 60% $C_{3+}$ hydrocarbons. The residue stream is only slightly enriched in hydrogen content, from 20% to 25%.

EXAMPLE 2

The calculation of Example 1 was repeated, but with a larger stage-cut and larger membrane area.

The results of the calculations are shown in Table 2. The stream numbers correspond to FIG. 1.

TABLE 2

| Component/Parameter | Stream 119 | Stream 122 | Stream 121 |
|---|---|---|---|
| Flow Rate (scfm) | 3,472 | 1,896 | 1,577 |
| Mass Flow Rate (lb/h) | 16,632 | 7,098 | 9,534 |
| Temperature (° C.) | 25 | 23 | 23 |
| Pressure (psia) | 75 | 75 | 15 |
| Component (mol %) | | | |
| Hydrogen | 20.0 | 30.0 | 8.0 |
| Methane | 15.0 | 20.9 | 8.0 |
| Ethane | 12.5 | 12.5 | 12.5 |
| Propane | 12.5 | 9.3 | 16.4 |
| n-Butane | 2.5 | 1.0 | 4.3 |
| n-Pentane | 2.5 | 0.8 | 4.6 |
| Ethylene | 10.0 | 9.1 | 11.0 |
| Propylene | 25.0 | 16.4 | 35.3 |

To perform this separation, 700 m² of membrane is needed, providing a stage-cut of 45%. The separation produces a permeate stream containing 46% olefins and about 60% $C_{3+}$ hydrocarbons. The residue stream is enriched in hydrogen content from 20% to 30%.

EXAMPLE 3

The calculation of Example 2 was repeated, but with a larger stage-cut and larger membrane area.

The results of the calculations are shown in Table 3. The stream numbers correspond to FIG. 1.

TABLE 3

| Component/Parameter | Stream 119 | Stream 122 | Stream 121 |
|---|---|---|---|
| Flow Rate (scfm) | 3,472 | 1,461 | 2,011 |
| Mass Flow Rate (lb/h) | 16,632 | 4,820 | 11,812 |
| Temperature (° C.) | 25 | 22 | 22 |
| Pressure (psia) | 75 | 75 | 15 |
| Component (mol %) | | | |
| Hydrogen | 20.0 | 35.0 | 9.1 |
| Methane | 15.0 | 23.5 | 8.8 |
| Ethane | 12.5 | 11.9 | 12.9 |
| Propane | 12.5 | 7.6 | 16.1 |
| n-Butane | 2.5 | 0.6 | 3.9 |
| n-Pentane | 2.5 | 0.4 | 4.0 |
| Ethylene | 10.0 | 8.3 | 11.2 |
| Propylene | 25.0 | 12.7 | 33.9 |

To perform this separation, 900 m² of membrane is needed, providing a stage-cut of 58%. The separation produces a permeate stream containing 45% olefins and just under 60% $C_{3+}$ hydrocarbons. The residue stream is enriched in hydrogen content from 20% to 35%.

EXAMPLE 4

The calculation of Example 3 was repeated, but with a larger stage-cut and larger membrane area.

The results of the calculations are shown in Table 4. The stream numbers correspond to FIG. 1.

TABLE 4

| Component/Parameter | Stream 119 | Stream 122 | Stream 121 |
|---|---|---|---|
| Flow Rate (scfm) | 3,472 | 1,137 | 2,335 |
| Mass Flow Rate (lb/h) | 16,632 | 3,281 | 13,351 |
| Temperature (° C.) | 25 | 22 | 22 |
| Pressure (psia) | 75 | 75 | 15 |
| Component (mol %) | | | |
| Hydrogen | 20.0 | 40.0 | 10.3 |
| Methane | 15.0 | 25.8 | 9.8 |
| Ethane | 12.5 | 10.9 | 13.3 |
| Propane | 12.5 | 6.0 | 15.7 |
| n-Butane | 2.5 | 0.4 | 3.5 |
| n-Pentane | 2.5 | 0.2 | 3.6 |
| Ethylene | 10.0 | 7.3 | 11.3 |
| Propylene | 25.0 | 9.5 | 32.6 |

To perform this separation, 1,100 m² of membrane is needed, providing a stage-cut of 65%. The separation produces a permeate stream containing 44% olefins and about 50% $C_{3+}$ hydrocarbons. The residue stream is enriched in hydrogen content from 20% to 40%.

EXAMPLE 5

Comparison of Examples 1–4

The data from Examples 1–4 are summarized in Tables 5A and 5B.

TABLE 5A

| Example # | Stage-Cut (%) | Membrane Area (m²) | Hydrogen Conc. in Residue (%) | Hydrogen Loss in Permeate (%) | $C_{3+}$ Loss in Residue (%) |
|---|---|---|---|---|---|
| (prior art) | — | — | 20 | — | 100 |
| 1 | 28 | 400 | 25 | 9 | 62 |
| 2 | 45 | 700 | 30 | 18 | 40 |
| 3 | 58 | 900 | 35 | 26 | 25 |
| 4 | 65 | 1,100 | 40 | 34 | 16 |

As can be seen from Table 5A, the greater the stage-cut, the greater is the hydrogen enrichment of the residue stream, but this is achieved at the expense of loss of hydrogen into the permeate stream.

TABLE 5B

| Example # | Stage-Cut (%) | Membrane Area (m²) | $C_{3+}$ Conc. in Permeate (%) | $C_{3+}$ Loss in Residue (%) | Hydrogen Loss in Permeate (%) |
|---|---|---|---|---|---|
| (prior art) | — | — | 33 | 100 | — |
| 1 | 28 | 400 | 64 | 62 | 9 |
| 2 | 45 | 700 | 61 | 40 | 18 |
| 3 | 58 | 900 | 58 | 25 | 26 |
| 4 | 65 | 1,100 | 55 | 16 | 34 |

As can be seen from Table 5B, the lower the stage-cut, the greater is the $C_{3+}$ hydrocarbon enrichment of the permeate stream, but this is achieved at the expense of loss of $C_{3+}$ hydrocarbons in the residue stream.

EXAMPLES 6–10

Effect of Lower Condensation Temperature

A set of computer calculations was performed to model the treatment of the overhead vapor stream from the absorption section of the catalytic cracking plant according to the embodiment of FIG. 2. The overhead stream was assumed to have the same composition and flow rate as in Examples 1–5, and the membrane properties were also assumed to be the same as in Examples 1–5. It was assumed that the stream was compressed to 200 psia in compressor 220, then cooled to different temperatures.

EXAMPLE 6

The stream was assumed to be cooled to 15° C. The results of the calculations are shown in Table 6. The stream numbers correspond to FIG. 2.

TABLE 6

| Component/ Parameter | Stream 219 | Stream 223 | Stream 224 | Stream 226 | Stream 227 |
| --- | --- | --- | --- | --- | --- |
| Mass Flow Rate (lb/h) | 16,632 | 1,791 | 14,841 | 11,227 | 3,614 |
| Temperature (° C.) | 25 | 15 | 15 | 5 | 5 |
| Pressure (psia) | 75 | 200 | 200 | 15 | 200 |
| Component (mol %) | | | | | |
| Hydrogen | 20.0 | 0.3 | 21.3 | 9.5 | 39.7 |
| Methane | 15.0 | 1.5 | 15.9 | 9.3 | 26.2 |
| Ethane | 12.5 | 6.3 | 12.9 | 13.7 | 11.7 |
| Propane | 12.5 | 20.1 | 12.0 | 16.0 | 5.7 |
| n-Butane | 2.5 | 11.1 | 1.9 | 3.0 | 0.2 |
| n-Pentane | 2.5 | 22.3 | 1.2 | 1.9 | — |
| Ethylene | 10.0 | 3.5 | 10.4 | 12.1 | 7.8 |
| Propylene | 25.0 | 34.8 | 24.3 | 34.4 | 8.7 |

— = less than 0.1
Membrane Area = 300 m$^2$
Theoretical Horsepower = 247 hp

In this case, three streams are produced from the absorber overhead. Stream 223, the condensate is mostly $C_{3+}$ hydrocarbons and is suitable to send to an olefin plant for olefin recovery. Stream 227, the residue stream contains 40% hydrogen, and could be further upgraded or sent as feed to a steam reformer, for example. Stream 226, the membrane permeate stream, contains 10% hydrogen and could be sent to the fuel line.

EXAMPLE 7

The calculations were repeated assuming that the stream was cooled to 5° C. The results are shown in Table 7. The stream numbers correspond to FIG. 2.

TABLE 7

| Component/ Parameter | Stream 219 | Stream 223 | Stream 224 | Stream 226 | Stream 227 |
| --- | --- | --- | --- | --- | --- |
| Mass Flow Rate (lb/h) | 16,632 | 4,172 | 12,460 | 9,559 | 2,901 |
| Temperature (° C.) | 25 | 5 | 5 | −5 | −5 |
| Pressure (psia) | 75 | 200 | 200 | 15 | 200 |
| Component (mol %) | | | | | |
| Hydrogen | 20.0 | 0.4 | 23.6 | 11.4 | 43.1 |
| Methane | 15.0 | 1.7 | 17.5 | 11.0 | 27.8 |
| Ethane | 12.5 | 7.8 | 13.4 | 14.9 | 10.9 |
| Propane | 12.5 | 22.8 | 10.6 | 14.6 | 4.3 |
| n-Butane | 2.5 | 9.5 | 1.2 | 1.9 | 0.1 |
| n-Pentane | 2.5 | 13.4 | 0.5 | 0.8 | — |

TABLE 7-continued

| Component/ Parameter | Stream 219 | Stream 223 | Stream 224 | Stream 226 | Stream 227 |
| --- | --- | --- | --- | --- | --- |
| Ethylene | 10.0 | 4.3 | 11.1 | 13.4 | 7.3 |
| Propylene | 25.0 | 40.1 | 22.2 | 32.0 | 6.6 |

— = less than 0.1
Membrane Area = 300 m$^2$
Theoretical Horsepower = 247 hp

Cooling to 5° C. instead of 15° C. increases the liquids recovery in stream 223 from 1,800 lb/h to 4,200 lb/h.

EXAMPLE 8

The calculations were repeated, assuming cooling to −5° C. The results are shown in Table 8. The stream numbers correspond to FIG. 2.

TABLE 8

| Component/ Parameter | Stream 219 | Stream 223 | Stream 224 | Stream 226 | Stream 227 |
| --- | --- | --- | --- | --- | --- |
| Mass Flow Rate (lb/h) | 16,632 | 6,930 | 9,702 | 7,590 | 2,112 |
| Temperature (° C.) | 25 | −5 | −5 | −15 | −15 |
| Pressure (psia) | 75 | 200 | 200 | 15 | 200 |
| Component (mol %) | | | | | |
| Hydrogen | 20.0 | 0.4 | 27.4 | 14.9 | 47.8 |
| Methane | 15.0 | 2.1 | 19.8 | 13.9 | 29.6 |
| Ethane | 12.5 | 9.6 | 13.6 | 16.2 | 9.4 |
| Propane | 12.5 | 23.6 | 8.3 | 11.8 | 2.6 |
| n-Butane | 2.5 | 7.4 | 0.6 | 1.0 | — |
| n-Pentane | 2.5 | 8.6 | 0.2 | 0.3 | — |
| Ethylene | 10.0 | 5.4 | 11.7 | 15.0 | 6.4 |
| Propylene | 25.0 | 42.9 | 18.3 | 26.9 | 4.0 |

— = less than 0.1
Membrane Area = 300 m$^2$
Theoretical Horsepower = 247 hp

Cooling to −5° C. increases liquids recovery to almost 7,000 lb/h. Also, the hydrogen concentration of the residue stream is significantly higher, at close to 50%.

EXAMPLE 9

The calculations were repeated, assuming cooling to −15° C. The results are shown in Table 9. The stream numbers correspond to FIG. 2.

TABLE 9

| Component/ Parameter | Stream 219 | Stream 223 | Stream 224 | Stream 226 | Stream 227 |
| --- | --- | --- | --- | --- | --- |
| Mass Flow Rate (lb/h) | 16,632 | 9,315 | 7,317 | 5,798 | 1,519 |
| Temperature (° C.) | 25 | −15 | −15 | −24 | −24 |
| Pressure (psia) | 75 | 200 | 200 | 15 | 200 |
| Component (mol %) | | | | | |
| Hydrogen | 20.0 | 0.4 | 32.0 | 19.6 | 52.7 |
| Methane | 15.0 | 2.6 | 22.6 | 17.6 | 31.0 |
| Ethane | 12.5 | 11.4 | 13.2 | 16.6 | 7.5 |
| Propane | 12.5 | 23.1 | 6.0 | 8.8 | 1.4 |
| n-Butane | 2.5 | 6.0 | 0.4 | 0.6 | — |
| n-Pentane | 2.5 | 6.4 | 0.1 | 0.1 | — |
| Ethylene | 10.0 | 6.6 | 12.1 | 16.1 | 5.2 |
| Propylene | 25.0 | 43.4 | 13.7 | 20.7 | 2.1 |

— = less than 0.1
Membrane Area = 300 m$^2$
Theoretical Horsepower = 247 hp

Liquids recovery is now 9,300 lb/h and the hydrogen content of the residue stream is over 50%.

EXAMPLE 10

Comparison of Examples 6–9

The data from Examples 6–9 are summarized in Table 10.

TABLE 10

| Example # | Condenser Temp. (° C.) | Hydrogen Conc. in Residue (%) | NGL Recovered (lb/h) |
|---|---|---|---|
| 6 | 15 | 39.7 | 1,791 |
| 7 | 5 | 43.1 | 4,172 |
| 8 | −5 | 47.8 | 6,930 |
| 9 | −15 | 52.7 | 9,315 |

EXAMPLES 11–15

Effect of Permeate Recycle

A set of computer calculations was performed using the same assumptions as in Examples 6–9. For these calculations, it was assumed that the treatment scheme was as in FIG. 4, with the permeate stream, 426, recirculated upstream of compressor 220.

EXAMPLE 11

Calculations were performed for the 15° C. case. The results are shown in Table 11. The stream numbers correspond to FIG. 4.

TABLE 11

| Component/Parameter | Stream 219 | Stream 223 | Stream 224 | Stream 426 | Stream 227 |
|---|---|---|---|---|---|
| Mass Flow Rate (lb/h) | 16,632 | 5,509 | 26,269 | 15,147 | 11,121 |
| Temperature (° C.) | 25 | 15 | 15 | 6 | 6 |
| Pressure (psia) | 15 | 200 | 200 | 15 | 200 |
| Component (mol %) | | | | | |
| Hydrogen | 20.0 | 0.3 | 15.7 | 5.2 | 25.1 |
| Methane | 15.0 | 1.2 | 12.4 | 5.5 | 18.6 |
| Ethane | 12.5 | 6.4 | 13.1 | 11.9 | 14.1 |
| Propane | 12.5 | 22.1 | 13.3 | 16.9 | 10.0 |
| n-Butane | 2.5 | 10.1 | 1.8 | 3.2 | 0.5 |
| n-Pentane | 2.5 | 11.7 | 0.6 | 1.3 | 0.1 |
| Ethylene | 10.0 | 4.0 | 11.9 | 12.3 | 11.6 |
| Propylene | 25.0 | 44.2 | 31.2 | 43.7 | 20.0 |

— = less than 0.1
Membrane Area = 300 m²
Theoretical Horsepower = 1,241 hp

EXAMPLE 12

Calculations were performed for the 5° C. case. The results are shown in Table 12. The stream numbers correspond to FIG. 4.

TABLE 12

| Component/Parameter | Stream 219 | Stream 223 | Stream 224 | Stream 426 | Stream 227 |
|---|---|---|---|---|---|
| Mass Flow Rate (lb/h) | 16,632 | 8,390 | 20,609 | 12,368 | 8,241 |
| Temperature (° C.) | 25 | 5 | 5 | −4 | −4 |
| Pressure (psia) | 15 | 200 | 200 | 15 | 200 |
| Component (mol %) | | | | | |
| Hydrogen | 20.0 | 0.3 | 18.8 | 7.0 | 29.8 |
| Methane | 15.0 | 1.5 | 14.8 | 7.4 | 21.7 |
| Ethane | 12.5 | 8.5 | 14.5 | 14.5 | 14.5 |
| Propane | 12.5 | 23.2 | 10.9 | 14.9 | 7.2 |
| n-Butane | 2.5 | 7.1 | 0.9 | 1.7 | 0.2 |
| n-Pentane | 2.5 | 7.5 | 0.3 | 0.5 | — |
| Ethylene | 10.0 | 5.4 | 13.8 | 15.5 | 12.3 |
| Propylene | 25.0 | 46.5 | 26.0 | 38.6 | 14.3 |

— = less than 0.1
Membrane Area = 300 m²
Theoretical Horsepower = 1,174 hp

EXAMPLE 13

Calculations were performed for the −5° C. case. The results are shown in Table 13. The stream numbers correspond to FIG. 4.

TABLE 13

| Component/Parameter | Stream 219 | Stream 223 | Stream 224 | Stream 426 | Stream 227 |
|---|---|---|---|---|---|
| Mass Flow Rate (lb/h) | 16,632 | 10,685 | 15,639 | 9,692 | 5,947 |
| Temperature (° C.) | 25 | −5 | −5 | −14 | −14 |
| Pressure (psia) | 15 | 200 | 200 | 15 | 200 |
| Component (mol %) | | | | | |
| Hydrogen | 20.0 | 0.3 | 22.8 | 9.8 | 35.2 |
| Methane | 15.0 | 1.9 | 17.8 | 10.2 | 25.1 |
| Ethane | 12.5 | 10.8 | 15.3 | 16.9 | 13.8 |
| Propane | 12.5 | 22.8 | 8.1 | 11.9 | 4.6 |
| n-Butane | 2.5 | 5.6 | 0.5 | 0.9 | 0.1 |
| n-Pentane | 2.5 | 5.7 | 0.1 | 0.3 | — |
| Ethylene | 10.0 | 7.1 | 15.6 | 19.1 | 12.2 |
| Propylene | 25.0 | 45.7 | 19.7 | 30.9 | 9.0 |

— = less than 0.1
Membrane Area = 300 m²
Theoretical Horsepower = 1,110 hp

EXAMPLE 14

Calculations were performed for the −15° C. case. The results are shown in Table 14. The stream numbers correspond to FIG. 4.

TABLE 14

| Component/Parameter | Stream 219 | Stream 223 | Stream 224 | Stream 426 | Stream 227 |
|---|---|---|---|---|---|
| Mass Flow Rate (lb/h) | 16,632 | 12,238 | 11,869 | 7,474 | 4,395 |
| Temperature (° C.) | 25 | −15 | −15 | −23 | −23 |
| Pressure (psia) | 15 | 200 | 200 | 15 | 200 |

TABLE 14-continued

| Component/Parameter | Stream 219 | Stream 223 | Stream 224 | Stream 426 | Stream 227 |
|---|---|---|---|---|---|
| Component (mol %) | | | | | |
| Hydrogen | 20.0 | 0.4 | 27.5 | 13.5 | 40.6 |
| Methane | 15.0 | 2.4 | 21.2 | 13.7 | 28.2 |
| Ethane | 12.5 | 12.9 | 15.0 | 18.1 | 12.0 |
| Propane | 12.5 | 21.8 | 5.7 | 9.0 | 2.7 |
| n-Butane | 2.5 | 4.8 | 0.3 | 0.6 | — |
| n-Pentane | 2.5 | 4.9 | 0.1 | 0.1 | — |
| Ethylene | 10.0 | 8.9 | 16.2 | 21.7 | 11.2 |
| Propylene | 25.0 | 43.8 | 14.0 | 23.4 | 5.3 |

— = less than 0.1
Membrane Area = 300 m$^2$
Theoretical Horsepower = 1,057 hp

EXAMPLE 15

Comparison of Examples 11–14 and 6–9

TABLE 15

| | Condenser | Hydrogen Conc. in Residue (%) | | LPG Recovered (lb/h) | | Additional Compressor |
|---|---|---|---|---|---|---|
| Example # | Temp. (° C.) | w/o recycle | w/ recycle | w/o recycle | w/ recycle | hp w/ recycle |
| 6/11 | 15 | 39.7 | 25.1 | 1,791 | 5,509 | 994 |
| 7/12 | 5 | 43.1 | 29.8 | 4,172 | 8,390 | 927 |
| 8/13 | −5 | 47.8 | 35.2 | 6,930 | 10,685 | 863 |
| 9/14 | −15 | 52.7 | 40.6 | 9,315 | 12,238 | 810 |

Recirculating the membrane permeate stream provides much better LPG recovery under otherwise similar conditions, but uses considerable extra compressor capacity, and reduces the hydrogen concentration in the residue.

EXAMPLE 16

A computer calculation was performed assuming the absorber overhead flow rate and composition. The treatment scheme was assumed to be as in FIG. 5, with that is, the membrane residue stream, 227, is sent to an additional treatment step, 528, and with the permeate stream from the first bank of modules recirculated to the compressor. The additional treatment was assumed to be permeation through a second bank of hydrogen-rejecting membranes. In another way, the design can be viewed as that of FIGS. 2 or 4, where the membrane separation step is a two-step operation. The membrane properties for both banks of membrane modules were assumed to be as in Example 1. The results of the calculations are shown in Table 16. The stream numbers correspond to FIG. 5.

TABLE 16

| Component/Parameter | Stream 219 | Stream 223 | Stream 224 | Stream 226 | Stream 227 | Stream 529 | Stream 530 |
|---|---|---|---|---|---|---|---|
| Mass Flow Rate (lb/h) | 16,632 | 10,685 | 15,637 | 9,691 | 5,946 | 4,019 | 1,927 |
| Temperature (° C.) | 25 | −5 | −5 | −14 | −14 | −21 | −21 |
| Pressure (psia) | 15 | 200 | 200 | 15 | 200 | 15 | 200 |
| Component (mol %) | | | | | | | |
| Hydrogen | 20.0 | 0.3 | 22.8 | 9.8 | 35.2 | 20.9 | 50.0 |
| Methane | 15.0 | 1.9 | 17.8 | 10.1 | 25.1 | 19.3 | 31.1 |
| Ethane | 12.5 | 10.8 | 15.3 | 16.9 | 13.8 | 18.6 | 8.8 |
| Propane | 12.5 | 22.8 | 8.1 | 11.9 | 4.6 | 7.5 | 1.5 |
| n-Butane | 2.5 | 5.6 | 0.5 | 0.9 | 0.1 | 0.2 | — |
| n-Pentane | 2.5 | 5.7 | 0.1 | 0.3 | — | — | — |
| Ethylene | 10.0 | 7.1 | 15.5 | 19.1 | 12.2 | 17.8 | 6.4 |
| Propylene | 25.0 | 45.7 | 19.7 | 31.0 | 9.0 | 15.5 | 2.2 |

— = less than 0.1
Membrane Area = 300 + 235 m$^2$
Theoretical Horsepower = 1,110 hp Using the second membrane step enables the hydrogen content of the residue stream to be raised to 50%. The permeate, 529, from the second membrane step contains 20% hydrogen and could be passed to the fuel gas line.

We claim:

1. A catalytic cracking process, comprising the following steps:

(a) cracking a hydrocarbon feedstock;

(b) fractionating the hydrocarbon product of step (a) to produce at least one liquid stream and an overhead vapor stream;

(c) cooling at least a part of the overhead vapor stream, thereby producing an overhead liquid stream and a wet gas stream;
(d) compressing at least a part of the wet gas stream;
(e) separating the compressed wet gas stream into a hydrocarbon liquid portion and a vapor portion;
(f) passing at least a part of the vapor portion through at least one absorption step to absorb $C_{3+}$ hydrocarbon components, thereby producing a lighter vapor portion;
(g) passing at least a part of the lighter vapor portion as a feed gas across the feed side of a polymeric membrane having a feed side and a permeate side and being selectively permeable to $C_{2+}$ hydrocarbons over hydrogen;
(h) withdrawing from the permeate side a permeate stream enriched in $C_{2+}$ hydrocarbons compared with the feed gas;
(i) withdrawing from the feed side a residue stream enriched in hydrogen compared with the feed gas.

2. The process of claim 1, further comprising subjecting the permeate stream to additional treatment to recover at least one hydrocarbon product.

3. The process of claim 2 wherein the hydrocarbon product comprises LPG.

4. The process of claim 2, wherein the hydrocarbon product comprises propylene.

5. The process of claim 2, wherein the hydrocarbon product comprises ethylene.

6. The process of claim 1, further comprising subjecting the residue stream to additional treatment to recover a hydrogen product stream.

7. The process of claim 6, wherein the additional treatment comprises pressure swing adsorption.

8. The process of claim 6, wherein the additional treatment step comprises membrane separation using a hydrogen-selective membrane.

9. The process of claim 1, further comprising compressing the part of the lighter vapor portion before passing it across the membrane.

10. The process of claim 9, further comprising cooling the part of the lighter vapor portion after compressing it, thereby condensing a liquid $C_{3+}$ hydrocarbon fraction, which is removed prior to passing the feed gas across the feed side.

11. The process of claim 1, wherein step (f) comprises two absorption steps in series, and wherein the lighter vapor portion is produced by the second absorption step.

12. The process of claim 1, wherein the membrane comprises silicone rubber.

13. The process of claim 1, wherein the membrane comprises a superglassy polymer.

14. The process of claim 1, wherein the membrane comprises a polyamide-polyether block copolymer.

15. A catalytic cracking process, comprising the following steps:
(a) cracking a hydrocarbon feedstock;
(b) fractionating the hydrocarbon product of step (a) to produce at least one liquid stream and an overhead vapor stream;
(c) cooling at least a part of the overhead vapor stream, thereby producing an overhead liquid stream and a wet gas stream;
(d) compressing at least a part of the wet gas stream;
(e) separating the compressed wet gas stream into a hydrocarbon liquid portion and a vapor portion;
(f) passing at least a part of the vapor portion through at least one absorption step to absorb $C_{3+}$ hydrocarbon components, thereby producing a lighter vapor portion;
(g) compressing and then cooling at least a part of the lighter vapor portion;
(h) separating the compressed, cooled lighter vapor portion into a recovered liquid stream and an uncondensed stream;
(i) passing the uncondensed stream as a feed gas across the feed side of a polymeric membrane having a feed side and a permeate side and being selectively permeable to $C_{2+}$ hydrocarbons over hydrogen;
(j) withdrawing from the permeate side a permeate stream enriched in $C_{2+}$ hydrocarbons compared with the feed gas;
(k) withdrawing from the feed side a residue stream enriched in hydrogen compared with the feed gas.

16. The process of claim 15, further comprising subjecting the recovered liquid stream to additional treatment to recover an olefin product, wherein the olefin product is chosen from the group consisting of ethylene and propylene.

17. The process of claim 15, further comprising subjecting the residue stream to additional treatment to recover a hydrogen product stream.

18. The process of claim 17, wherein the additional residue treatment comprises pressure swing adsorption.

19. The process of claim 15, wherein the membrane comprises silicone rubber.

20. The process of claim 15, wherein the membrane comprises a superglassy polymer.

21. The process of claim 15, wherein the membrane comprises a polyamide-polyether block copolymer.

22. The process of claim 15, wherein the permeate stream is recirculated to step (g).

23. A process for treating a gas stream, containing hydrogen and $C_{3+}$ hydrocarbons, from a catalytic cracking plant, comprising the steps of:
(a) contacting the gas stream with a hydrocarbon liquid such that $C_{3+}$ hydrocarbons contained in the gas stream are absorbed into the hydrocarbon liquid, leaving a lighter gas stream depleted in $C_{3+}$ hydrocarbons compared with the gas stream;
(b) passing the lighter gas stream as a feed gas across the feed side of a polymeric membrane having a feed side and a permeate side and being selectively permeable to $C_{3+}$ hydrocarbons over hydrogen;
(c) withdrawing from the permeate side a permeate stream enriched in $C_{3+}$ hydrocarbons compared with the feed gas;
(d) withdrawing from the feed side a residue stream enriched in hydrogen compared with the feed gas;
(e) passing the permeate stream to a further treatment step to produce at least one hydrocarbon product.

24. The process of claim 23, wherein the further treatment step comprises condensation.

25. The process of claim 23, wherein the further treatment step comprises distillation.

26. The process of claim 23, wherein the further treatment step comprises olefin/paraffin splitting.

27. The process of claim 23, wherein the hydrocarbon product comprises LPG.

28. The process of claim 23, wherein the hydrocarbon product comprises an olefin selected from the group consisting of ethylene and propylene.

29. The process of claim 23, further comprising subjecting the residue stream to additional treatment to recover a hydrogen product stream.

30. The process of claim 29, wherein the additional residue treatment comprises pressure swing adsorption.

31. The process of claim 23, wherein the membrane comprises silicone rubber.

32. The process of claim 23, wherein the membrane comprises a superglassy polymer.

33. The process of claim 23, wherein the membrane comprises a polyamide-polyether block copolymer.

34. A process for treating a gas stream, containing hydrogen and $C_{3+}$ hydrocarbons from a catalytic cracking plant, comprising the steps of:

(a) contacting the gas stream with a hydrocarbon liquid such that $C_{3+}$ hydrocarbons contained in the gas stream are absorbed into the hydrocarbon liquid, leaving a lighter gas stream depleted in $C_{3+}$ hydrocarbons compared with the gas stream;

(b) compressing and then cooling at least a part of the lighter gas stream;

(c) separating the compressed, cooled lighter gas stream into a recovered liquid stream and an uncondensed stream;

(d) passing the uncondensed stream as a feed gas across the feed side of a polymeric membrane having a feed side and a permeate side and being selectively permeable to $C_{3+}$ hydrocarbons over hydrogen;

(e) withdrawing from the permeate side a permeate stream enriched in $C_{3+}$ hydrocarbons compared with the feed gas;

(f) withdrawing from the feed side a residue stream enriched in hydrogen compared with the feed gas;

(g) passing the permeate stream to a further treatment step to produce at least one hydrocarbon product.

35. The process of claim 34, further comprising subjecting the recovered liquid stream to additional treatment to recover an olefin product, wherein the olefin product is chosen from the group consisting of ethylene and propylene.

36. The process of claim 34, further comprising subjecting the residue stream to additional treatment to recover a hydrogen product stream.

37. The process of claim 36, wherein the additional residue treatment comprises pressure swing adsorption.

38. The process of claim 34, wherein the membrane comprises silicone rubber.

39. The process of claim 34, wherein the membrane comprises a superglassy polymer.

40. The process of claim 34, wherein the membrane comprises a polyamide-polyether block copolymer.

41. The process of claim 34, wherein the permeate stream is recirculated to step (b).

42. A catalytic cracking process, comprising the following steps:

(a) cracking a hydrocarbon feedstock;

(b) fractionating the hydrocarbon product of step (a) to produce at least one liquid stream and an overhead vapor stream;

(c) cooling at least a part of the overhead vapor stream, thereby producing an overhead liquid stream and a wet gas stream;

(d) compressing at least a part of the wet gas stream;

(e) separating the compressed wet gas stream into a hydrocarbon liquid portion and a vapor portion;

(f) passing at least a part of the vapor portion as a feed gas across the feed side of a polymeric membrane having a feed side and a permeate side and being selectively permeable to $C_{2+}$ hydrocarbons over hydrogen;

(g) withdrawing from the permeate side a permeate stream enriched in $C_{2+}$ hydrocarbons compared with the feed gas;

(h) withdrawing from the feed side a residue stream enriched in hydrogen compared with the feed gas;

(i) passing the permeate stream to a further treatment step to produce at least one hydrocarbon product.

43. The process of claim 42, wherein the further treatment step comprises condensation.

44. The process of claim 42, wherein the further treatment step comprises distillation.

45. The process of claim 42, wherein the further treatment step comprises olefin/paraffin splitting.

46. The process of claim 42, wherein the hydrocarbon product comprises LPG.

47. The process of claim 42, wherein the hydrocarbon product comprises an olefin selected from the group consisting of ethylene and propylene.

48. The process of claim 42, further comprising subjecting the residue stream to additional treatment to recover a hydrogen product stream.

49. The process of claim 48, wherein the additional residue treatment comprises pressure swing adsorption.

50. The process of claim 42, wherein the membrane comprises silicone rubber.

51. The process of claim 42, wherein the membrane comprises a superglassy polymer.

52. The process of claim 42, wherein the membrane comprises a polyamide-polyether block copolymer.

53. A process for treating an overhead gas stream, containing hydrogen and $C_{2+}$ hydrocarbons, from an absorption column of a catalytic cracking plant, comprising the steps of:

(a) withdrawing the gas stream from the column;

(b) passing the gas stream as a feed gas across the feed side of a polymeric membrane having a feed side and a permeate side and being selectively permeable to $C_{2+}$ hydrocarbons over hydrogen;

(c) withdrawing from the permeate side a permeate stream enriched in $C_{2+}$ hydrocarbons compared with the feed gas;

(d) withdrawing from the feed side a residue stream enriched in hydrogen compared with the feed gas;

(e) passing the permeate stream to a further treatment step to produce at least one hydrocarbon product, wherein the further treatment step is selected from the group consisting of condensation, distillation, and olefin/paraffin splitting.

* * * * *